Figure 1:
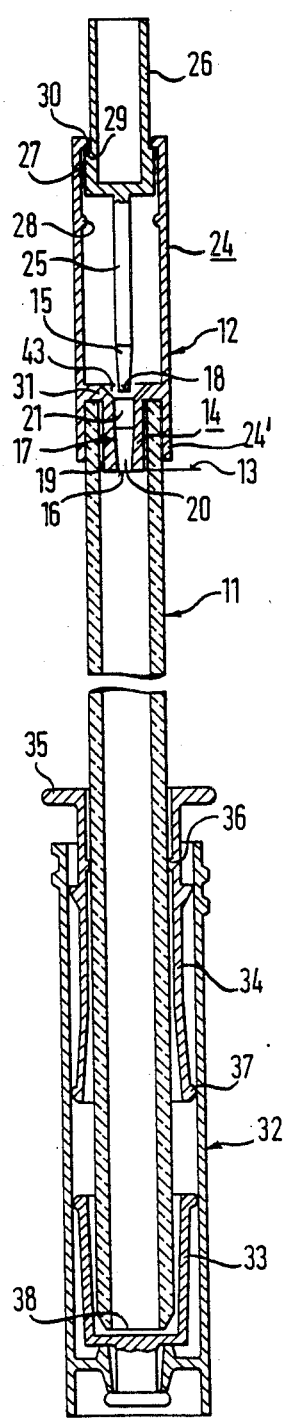

United States Patent [19]

Sarstedt

[11] Patent Number: 4,648,265
[45] Date of Patent: Mar. 10, 1987

[54] BLOOD SEDIMENTATION APPARATUS

[75] Inventor: Walter Sarstedt, Nümbrecht-Rommelsdorf, Fed. Rep. of Germany

[73] Assignee: Walter Sarstedt Kunststoff-Spritzgusswerk, Rommelsdorf, Fed. Rep. of Germany

[21] Appl. No.: 743,541

[22] Filed: Jun. 11, 1985

[30] Foreign Application Priority Data

Jun. 13, 1984 [DE] Fed. Rep. of Germany ....... 3421955

[51] Int. Cl.⁴ ............................................ G01N 33/48
[52] U.S. Cl. ...................................... 73/61.4; 604/231
[58] Field of Search ................... 73/61.4, 53, 864.13, 73/864.16; 210/927, 514, 95; 128/632, 637, 765; 604/207, 218, 231

[56] References Cited

U.S. PATENT DOCUMENTS

| | | | |
|---|---|---|---|
| 3,660,037 | 5/1972 | Sokol | 73/61.4 |
| 4,037,464 | 7/1977 | Wenander | 73/61.4 |
| 4,197,735 | 4/1980 | Munzer et al. | 73/6 |
| 4,353,246 | 10/1982 | Farber et al. | 73/61.4 |
| 4,427,015 | 1/1984 | Redeaux, Jr. | 128/765 |
| 4,519,402 | 5/1985 | Andersen | 128/765 |

FOREIGN PATENT DOCUMENTS

| 257062 | 8/1912 | Fed. Rep. of Germany | 604/218 |
|---|---|---|---|
| 2915465 | 10/1980 | Fed. Rep. of Germany | 128/765 |

Primary Examiner—Jerry W. Myracle
Assistant Examiner—Hezron E. Williams
Attorney, Agent, or Firm—Townsend & Townsend

[57] ABSTRACT

A blood sedimentation apparatus has an upright transparent sedimentation tube (11) which can be inserted into a sample container (32) containing blood and which can filled with blood up to a zero mark (13) provided in the upper region by displacing the blood contained in the sample container. A closure (12), which includes an overflow vessel (24) and a hollow spigot (14) which communicates therewith, and which extends from above into the sedimentation tube up to the zero mark (13) can be placed onto the upper end of the sedimentation tube (11). A closure member (15) which closes the opening (16) of the hollow spigot (14) can be introduced axially into the hollow spigot (14).

19 Claims, 6 Drawing Figures

U.S. Patent    Mar. 10, 1987    Sheet 1 of 2    4,648,265

BLOOD SEDIMENTATION APPARATUS

The invention relates to a blood sedimentation apparatus comprising an upright transparent sedimentation tube which is open at the top and at the bottom, which can be positioned in a sample container containing blood and which can be filled with blood up to a zero mark in the upper region by displacement of the blood contained in the container.

Such blood sedimentation tubes are placed, for the purpose of carrying out a blood sedimentation, into the sample container containing the blood, whereupon the blood is displaced into the interior of the sedimentation tube, where it ultimately climbs up to the zero mark. Displacement of the blood into the sedimentation tube is effected either by means of an annular piston, on depressing the piston, or by means of a lower part of the sample container, which is dimensioned in correspondence with the outer diameter of the sedimentation tube, on insertion of the sedimentation tube. Even when the operator is very careful it is frequently not possible to exactly position the level of the blood within the sedimentation tube at the zero mark.

The object of the invention is thus to provide a blood sedimentation apparatus of the initially named kind by means of which the column of blood inside the sedimentation tube can be faithfully and reliably adjusted to the zero mark in the upper region of the sedimentation tube without particular attentiveness of the part of the operator.

In order to satisfy this object the invention provides that a closure can be placed onto the upper end of the sedimentation tube; that the closure includes an overflow vessel and a hollow spigot which communicates with the overflow vessel, which is sealed at the top relative to the sedimentation tube and which extends into the sedimentation tube up to the zero mark; and that a closure member can be axially inserted into the hollow spigot in order to close the opening of the hollow spigot which lies in the sedimentation tube.

As a result of this construction one proceeds on pushing the blood into the sedimentation tube in such a way that after positioning of the closure the blood column rises noticably above the zero mark and the blood flows in right up to the overflow vessel. If the closure member is now pushed into the hollow spigot then the blood displaced into the overflow vessel is separated from the blood located in the sedimentation tube by the closure member which lies flush with the opening of the hollow spigot, and thus with the zero mark. The effective blood column used for the blood sedimentation now ends exactly at the zero mark so that a sedimentation of the blood can be carried out without problem. No particular care and attentiveness of the operator is required for the precise dimensioning of the length of the blood column as a result of the fact that one can first allow the blood column to rise significantly above the zero mark, and that the correct length of the blood column can subsequently be brought about simply by putting in the closure member. It is however important that the closure be constructed in such a way that the lower end of the hollow spigot comes to rest exactly at the level of the zero mark of the sedimentation tube after placing the closure on the upper end of the sedimentation tube. This can for example be realised in simple manner by providing a transverse wall at the upper end of the hollow spigot with the transverse wall simultaneously forming the base of the overflow vessel.

A first advantageous embodiment is characterised in that the internal bore of the hollow spigot is constructed to taper towards the opening, at least in the region of this opening; and in that the closure member is fomed as a spigot which tapers in a complementary manner thereto such that when the spigot is inserted from above its lower end is flush with the opening, and such that a gap which allows the blood to pass in the axial direction is left between the preferably cylindrical regions which adjoin the tapering regions of the internal bore and of the spigot respectively. As a result of this construction it is ensured that the closure member can be effortlessly introduced into the internal bore of the hollow spigot and that excess pressure in the column of blood is not generated by a piston-like action. It is important for troublefree functioning of the sedimentation apparatus that the hollow spigot either externally sealingly contacts the interior wall of the sedimentation tube on all sides, so that no blood can stand above the zero mark in the sedimentation tube, or so that air present around the hollow spigot cannot escape upwardly.

It is however also possible that the internal bore of the hollow spigot is constructed to broaden towards the opening at least in the region of the opening; and that the closure member is constructed as a spigot which broadens in complementary manner thereto such that on inserting the spigot from below its lower end is flush with the opening, and such that a gap which allows the blood to pass in the axial direction is left between the preferably cylindrical regions adjoining the broadened regions of the internal bore and of the spigot respectively. In this case the closure member is brought into the closed position by drawing it upwardly.

A further practical realisation of the inventive thought is characterised in that abutments are provided at the opening of the internal bore of the hollow spigot for a closure plug which is introduced from above or from below, with the lower surface of the inserted closure plug lying flush with the opening.

A further development of the invention was constructed for the simple actuation of the closure member from the outside in such a way that the closure member is connected with an actuating piston via an actuating rod, with the actuating piston being axially displaceable within the overflow vessel and projecting upwardly beyond the overflow vessel for actuation. In order that no excess pressure is created in the overflow vessel on depressing the piston the invention envisages that a vent is provided between the interior of the overflow vessel and the atmosphere in or at the actuating piston.

In order to secure the closure member in the closed position a further embodiment envisages that a latch projection is provided at the inner wall of the overflow vessel and engages, when the closure member is lcoated in the closed position, behind an upper ring step of the piston and thereby secures the latter in the closed position. The retracted position of the actuating piston can be restricted by the ring step contacting a radially inwardly projecting collar of the overflow vessel when the closure member is located in the open position.

A very compact realisation of the inventive thought, which is also suitable for a closure arrangement of several sedimentation tubes alongside one another, is characterised in that the overflow vessel is of right cylindrical construction and in that its wall extends downwardly, at least over a part of the length of the hollow spigot, and in this region surrounds the upper end of the sedimentation tube in the form of a wall piece.

A further advantageous embodiment is characterised in that the hollow spigot projects downwardly from a transverse wall which is provided in the base of the overflow vessel and which has a central opening.

It is particularly favourable from the technical manufacturing viewpoint for the overflow vessel to be formed in one piece with the transverse wall, the hollow spigot and optionally with the wall piece. Moreover, for this purpose, the closure member can be formed in one piece with the actuating piston and optionally with the actuating rod.

It is important for troublefree blood sedimentation that no blood can be present above the opening of the hollow spigot, i.e. at the side of the hollow spigot above the zero mark, which could disturb the blood sedimentation by increasing the column above the zero mark. In order to achieve this a first practical embodiment provides that the hollow spigot lies in sealing contact around the inner wall of the sedimentation tube, at least at the level of the opening.

It is however also possible for one or more air gaps to be present around the hollow spigot with the air gaps being sealed against the outside by the closure. This can be realised most simply if the wall piece and/or the transverse wall sealingly contacts the outer wall or the upper end wall of the sedimentation tube.

Figure 2:
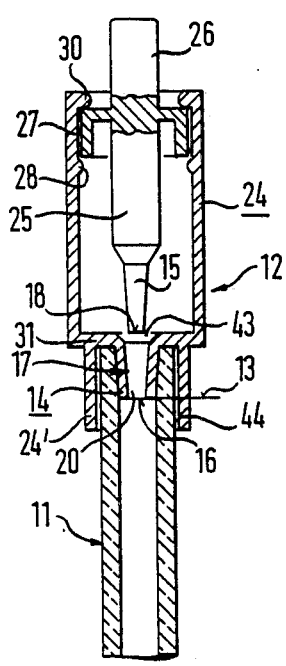
Figure 3:
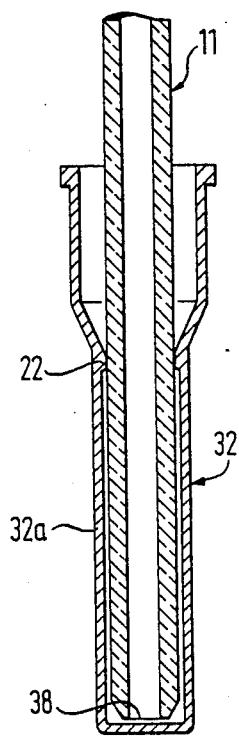
Figure 4:
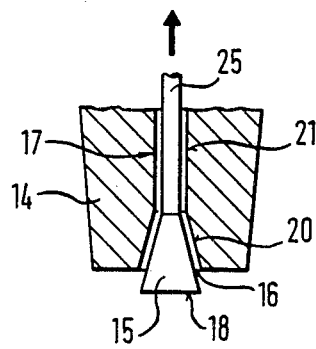
Figure 5:
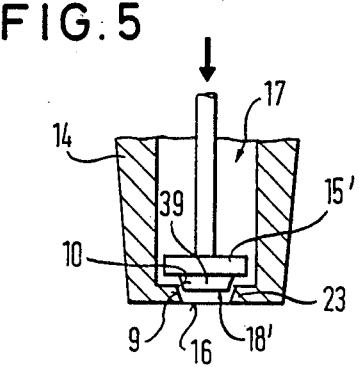
Figure 6:
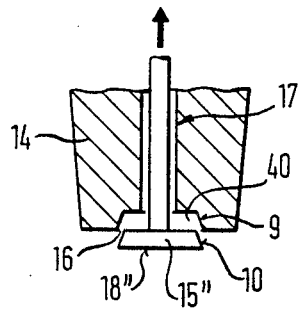

The invention will now be described in the following by way of example and with reference to the drawings which show:

FIG. 1 a partially sectioned sideview of a blood sedimentation apparatus in accordance with the invention, FIG. 2 a partially sectioned sideview of only the upper region of a further embodiment, FIG. 3 a partially sectioned sideview of only the lower region of a further embodiment of the sample container, which can be used both with the embodiment of FIG. 1 and also with the embodiment of FIG. 2, FIG. 4 an enlarged partial sideview of another embodiment of the closure in accordance with the invention, FIG. 5 a further realisation of the closure in accordance with the invention, and FIG. 6 a further modified embodiment of the closure of the invention.

In accordance with FIG. 1 a transparent right-cylindrical sedimentation tube 11 is arranged in a right cylindrical sample container 32 which has a substantially larger diameter and which is constructed as a blood extraction device with a piston 33. Prior to insertion of the sedimentation tube 11 blood has been tapped from a patient with this blood extraction device by retraction of the piston 33 and this blood is now located in the sample container 32.

A cylindrical piston 34 with an upwardly projecting actuating part 35 is arranged around the lower region of the sedimentation tube 11. The actuating part 35 is guided in a sealing sliding seat at the top at 36 on the sample tube 11 and at the bottom at 37 on the inner wall of the sample container 32. On depressing the piston 34 the blood located in the sample container 32 is forced through the lower opening 38 of the sedimentation tube 11 into the latter where it rises upwardly. The zero mark 13 up to which the blood column should extend is provided in the upper region of the sedimentation tube 11.

A closure 12 is placed onto the upper end of the sedimentation tube 11. The closure 12 consists of a right-cylindrical overflow vessel 24 the inner diameter of which corresponds approximately to the outer diameter of the sedimentation tube 11 and the cylindrical wall of which extends downwardly beyond a transverse wall 31 into a right-cylindrical wall piece 24' which sealingly surrounds the upper region of the sedimentation tube 11 at the outside, while the transverse wall 31 sits at the top on the end wall of the sedimentation tube 11, and thus determines the axial position of the closure 12 relative to the sedimentation tube 11. The overflow vessel 24 is thus advantageously approximately flush with the sedimentation tube 11 in the radial direction, i.e. it projects radially outwardly beyond the sedimentation tube only by its wall thickness. The transverse wall 31 has a funnel-like bore 43 at its center from which a hollow spigot 14 branches off downwardly, with the internal bore 17 of the hollow spigot being cylindrical in the upper region 21 and tapering conically in the lower region 20. The hollow spigot 14 extends in the mounted state of the closure 12, when the transverse wall 31 abuts against the upper end of the sedimentation tube 11, into the blood sedimentation tube 11 while leaving a narrow annular air gap 19, and indeed right up to the zero mark 13 where the opening 16 of the internal bore 17 is located.

An actuating piston 16 is vertically displaceably arranged in the upper region of the overflow vessel 24 and is connected via a cylindrical actuating rod 25, which is made as thin as possible in order to provide a volume which is as large as possible in the overflow vessel 24, with a spigot 15, which is of complementary shape to the conical region 20 of the internal bore 17.

A vent gap 27 is located between a broadened region of the actuating piston 26 which extends downwardly via a ring step (or annular shoulder) 29 and the internal wall of the overflow vessel 24. At the upper end the overflow vessel 24 has a radially inwardly extending collar 30 which engages behind the annular shoulder 29 of the actuating piston 26 when the spigot 15 is retracted. An annular radially inwardly projecting latch cam 28 is located beneath the retracted actuating piston 26 at the inner wall of the overflow vessel 24 and the broadened part of the actuating piston 26 can be forced past the latch cam 28, on depressing the actuating piston 26, until the latch cam 28 snaps behind the ring step 29. In this state the lower end surface 18 of the conical spigot 15 is aligned with the opening 16 of the internal bore 17 of the hollow spigot 14. In the depressed state of the actuating piston 26 the spigot 15 sealingly contacts the conical region 20 of the internal bore 17 on all sides. A ring gap through which the blood displaced on lowering the spigot 15 can climb upwardly into the overflow vessel 24 is present between the cylindrical region 21 and the bore 43 on the one side, and between the actuating rod 25 and the spigot 15 on the other side.

The operation of the described blood sedimentation apparatus proceeds as follows:

First of all the closure 12 is sealingly placed onto the sedimentation tube 11 into the position shown in FIG. 1 with the actuating piston 26 being located in the upper end position. The cylindrical piston 34 is pushed onto the sedimentation tube 11 from below. The sedimentation tube 11 is now inserted into the sample container 32 until it reaches the position shown in FIG. 1. If the piston 34 is now moved downwardly then a column of blood rises upwardly in the sedimentation tube 11 until it reaches the hollow spigot 14 and passes through this into the overflow vessel 24. As soon as this is the case, which can be achieved by a relatively coarse actuation of the piston 34, the downward movement of the piston 34 is terminated and the actuating piston 26 is moved downwardly from the top beyond the ring cam 28 until the end face 18 lies flush with the opening 16 and the ring step 29 has locked into place behind the ring cam 28. The blood located in the sedimentation tube is now separated from the blood located in the overflow vessel 24 and a blood column is present which extends upwardly exactly to the zero mark 13. It is important that the air gap 19 around the hollow spigot 14 is sealed at the top so that no blood can enter this place and forcify the blood sedimentation.

In the following figures the same reference numerals designate corresponding parts to those of FIG. 1.

In distinction to FIG. 1 the entire internal bore 17 of the embodiment of FIG. 2 is formed as a conical region 20 and a conical spigot 15 which extends over the full length of the hollow spigot 14 corresponds thereto.

In the embodiment of FIG. 2 the diameter of the overflow vessel 24 is somewhat larger than that of the sedimentation tube 11. An air gap 44 is located between the wall piece 24' and the sedimentation tube 11 so that on placing the closure 12 onto the sedimentation tube 11 the air displaced at the upper end of the hollow spigot 14 can escape. For this purpose the hollow spigot 14 sealingly contacts the inner wall of the sedimentation tube on all sides.

The actuating rod 25 is provided with a larger diameter comparted to that of FIG. 1 because the volume of the overflow vessel 24 is in any event sufficiently large due to the enlarged diameter.

At the bottom the sedimentation tube 11 is positioned, as shown in FIG. 1, in a sample container 32 formed as a blood extraction device.

The sample container 32 could also be constructed in the two embodiments of FIGS. 1 and 2 in the same way as shown in FIG. 3, i.e. could have a lower cylindrical region 32a corresponding substantially to the outer diameter of the sedimentation tube 11 with an inwardly projecting ring seal lip 22 at the top, with the sedimentation tube 11 being inserted from above into the lower cylindrical region 32a and with the blood located in the lower region 32a being forced into the interior of the sedimentation tube 11.

FIG. 4 shows another embodiment of the hollow spigot 14 which is again pressed in the manner of a plug into the upper end of the sedimentation tube 11. In place of a spigot which tapers conically from the top downwardly a spigot 15 is provided which broadens conically from the top downwardly and which cooperates with a correspondingly widening region 20 of the internal bore 17 of the hollow spigot 14. Closure is effected in this case by moving the spigot 15 upwardly in the direction of the arrow 4 until the lower surface 18 of the spigot 15 is flush with the opening 16 of the internal bore 17.

FIG. 5 shows an embodiment of the hollow spigot 14 with a substantially right cylindrical internal bore 17 and an annular inwardly projecting ring abutment 23 at its lower end onto which a correspondingly circular shaped closure plug 15' can be placed, with the closure plug 15' carrying a projection 39 which enters into the central opening of the ring-like abutment 23. The cooperating ring surfaces 9, 10 of the abutment 23 and of the projection 39 are again slightly conically shaped. The lower end surface 18' of the closure plug 15' lies flush with the opening 16 of the internal bore 17 in the closed state. Closing takes place in this embodiment in the direction of the arrow in FIG. 5.

FIG. 6 shows a similar embodiment in which however the closure plug 11 can be drawn from below into a ring-like enlargement 40 of the internal bore 17 in the direction of th arrow in such a way that the lower surface 18" of the closure plug 15' is flush with the opening 16 of the internal bore 17 in the sedimentation tube 11.

The conical surfaces 9, 10 of FIGS. 5 and 6 contact one another in the closed state.

The zero mark 13 is located at a level of approximately 200 mm. This desired height can be accurately maintained through the closure 12 of the invention.

The cone angle of the spigot 15 and of the conical region 20 is so small that the sealing of the closure 12 is first realised in the last instant of the closing movement. Up till then the displaced blood should be able to flow away upwardly into the overflow vessel 24.

A substantial advantage of the hermetic closure at the upper end of the sedimentation tube 11 through the closure 12 of the invention lies in the fact that the blood column does not drop in the event of a lack of sealing in the lower region of the sedimentation tube, in particular within the sample container 32. Evaporation of liquid at the upper end of the blood column located in the sedimentation tube 11 is also no longer possible through the hermetic closure at the upper end.

The internal bore 17 of the hollow spigot 14 has a diameter of substantially more than 1 mm, i.e. has practically no capillary action so that it can also be manufactured in desired lengths without great expense.

The essential advantage of the invention lies in the fact that, through the relatively large reservoir in the overflow vessel 24, the blood in the sample container 32 at the foot of the sedimentation tube 11 no longer needs to be so accurately pre-measured.

Air inclusions in the sample container 32 can also no longer deleteriously affect the blood sedimentation due to the closure in accordance with the invention.

What is claimed is:

1. Blood sedimentation apparatus for use with a sample container for containing blood, comprising:
    an upright transparent sedimentation tube having an upper region and being open at the top and at the bottom and positioned in the sample container containing blood and which can be filled with blood up to a zero mark in the upper region of the sedimentation tube by displacement of the blood contained in the sample container;
    a closure placed on the upper end of the sedimentation tube and sealingly closing said sedimentation tube at said upper end, the closure including:
    an overflow vessel;
    a hollow spigot communicating with the overflow vessel, extending into the sedimentation tube up to the zero mark, and having a lower opening which lies in the sedimentation tube at the level of the zero mark; and
    closure member which can be axially inserted into the hollow spigot to such an extent that its lower end is flush with the lower opening in order to close the lower opening of the hollow spigot when the closure member is inserted and to provide a blood column in said sedimentation tube extending exactly up to said zero mark.

2. Blood sedimentation apparatus in accordance with claim 2, wherein the internal bore of the hollow spigot is constructed to taper towards the opening of the hollow spigot which lies in the sedimentation tube, at least in a region of the bore of the hollow spigot adjacent this opening; the closure member being formed as a spigot which tapers in a complementary manner thereto such that when the spigot is inserted from above its lower end is flush with the opening of the hollow spigot, and such that a gap which allows the blood to pass in the axial direction is left between the preferably cylindrical regions adjoining the tapering regions of the internal bore and of the spigot respectively.

3. Blood sedimentation apparatus in accordance with claim 1, characterised in that the internal bore (17) of the hollow spigot (14) is constructed to broaden towards the opening (16) at least in the region (20) of the opening (16); and in that the closure member is constructd as a spigot (15) which broadens in complementary manner thereto such that on inserting the spigot (15) from below its lower end (18) is flush with the opening (16), and such that a gap which allows the blood to pass in the axial direction is left between the preferably cylindrical regions (21, 25) adjoining the broadened regions (20, 15) of the internal bore (17) and of the spigot (15) respectively.

4. Blood sedimentation apparatus in accordance claim 1, wherein abutments are provided at the opening of the internal bore of the hollow spigot for a closure plug which is introduced from below, with the lower surface of the inserted closure plug lying flush with the opening.

5. Blood sedimentation apparatus in accordance claim 1, characterised in that the closure member (15, 15', 15") is connected with an actuating piston (26) via an actuating rod (25), with the actuating piston (26) being axially displaceable within the overflow vessel (24) and projecting upwardly beyond the overflow vessel (24) for actuation.

6. Blood sedimentation apparatus in accordance with claim 5, wherein a vent is provided between the interior of the overflow vessel and the actuating piston.

7. Blood sedimentation apparatus in accordance with claim 5, characterised in that a latch projection (28) is provided at the inner wall of the overflow vessel and engages, when the closure member (15, 15', 15") is located in the closed position, behind an uppe ring ste (29) of the piston and thereby secures the latter in the closed position.

8. Blood sedimentation apparatus in accordance with claim 7, wherein the upper ring step of the piston contacts a radially inwardly projecting collar of the overflow vessel when the closure member is located in the open position.

9. Blood sedimentation apparatus in accordance with claim 1, characterised in that the overflow vessel (24) is of right-cylindrical construction; and in that its wall extends downwardly, at least over a part of the length of the hollow spigot (14), and in this region surrounds the upper end of the sedimentation tube (11) in the form of a wall piece (24').

10. Blood sedimentation apparatus in accordance with claim 9, wherein the hollow spigot projects downwardly from a transverse wall which is provided in the overflow vessel and which has a central opening.

11. Blood sedimentation apparatus in accordance with claim 10, wherein the overflow vessel is formed in one piece with the transverse wall, the hollow spigot and with the wall piece.

12. Blood sedimentation apparatus in accordance with claim 5, wherein the closure member is formed in one piece with the actuating piston and with the actuating rod.

13. Blood sedimentation apparatus in accordance with claim 1, characterised in that the hollow spigot (14) lies in sealing contact around the inner wall of the sedimentation tube (11), at least at the level of the opening (16).

14. Blood sedimentation apparatus in accordance with one of the claims 1, characterised in that one or more air gaps (19) are present around the hollow spigot (14) which are sealed against the outside by the closure (12).

15. Blood sedimentation apparatus in accordance with claim 9, characterised in that the wall piece (24') sealingly contacts the outer wall.

16. Blood sedimentation apparatus in accordance with claim 10, characterised in that the transverse wall (31) sealingly contacts the upper end wall of the sedimentation tube (11).

17. Blood sedimentation apparatus in accordance with claim 10, wherein the overflow vessel is formed in one piece with the transverse wall and the hollow spigot.

18. Blood sedimentation apparatus in accordance with claim 5, characterised in that the closure member is formed in one piece with the actuating piston.

19. Blood sedimentation apparatus in accordance with claim 1, wherein abutments are provided at the opening of the internal bore of the hollow spigot for a closure plug which is introduced from above, with the lower surface of the inserted closure plug lying flush with the opening.

* * * * *